(12) United States Patent
Bünger

(10) Patent No.: US 11,759,348 B2
(45) Date of Patent: Sep. 19, 2023

(54) DEVICE FOR HYPERTHERMIA TREATMENT OF ITCHING

(71) Applicant: DERMAPHARM AG, Grünwald (DE)

(72) Inventor: Daniel Bünger, Mönchengladbach (DE)

(73) Assignee: DERMAPHARM AG, Grünwald (DE)

( * ) Notice: Subject to any disclaimer, the term of this patent is extended or adjusted under 35 U.S.C. 154(b) by 656 days.

(21) Appl. No.: 16/317,147

(22) PCT Filed: Jul. 12, 2017

(86) PCT No.: PCT/EP2017/067544
§ 371 (c)(1),
(2) Date: Jan. 11, 2019

(87) PCT Pub. No.: WO2018/011263
PCT Pub. Date: Jan. 18, 2018

(65) Prior Publication Data
US 2019/0290477 A1    Sep. 26, 2019

(30) Foreign Application Priority Data

Jul. 12, 2016  (EP) ..................................... 16179093
Oct. 11, 2016  (EP) ..................................... 16193220

(51) Int. Cl.
*A61F 7/00* (2006.01)
*A61F 7/02* (2006.01)

(52) U.S. Cl.
CPC ................ *A61F 7/007* (2013.01); *A61F 7/02* (2013.01); *A61F 2007/0052* (2013.01); *A61F 2007/0071* (2013.01); *A61F 2007/0086* (2013.01); *A61F 2007/0087* (2013.01); *A61F 2007/0088* (2013.01); *A61F 2007/0093* (2013.01);
(Continued)

(58) Field of Classification Search
CPC .............. A61F 2007/0052; A61F 7/007; A61F 2007/0071; A61F 2007/0086; A61F 2007/0087; A61F 2007/0088; A61F 2007/0093; A61F 2007/0095; A61F 2007/0096; A61F 7/02; A61F 2007/00282; A61F 2007/00284
See application file for complete search history.

(56) References Cited

U.S. PATENT DOCUMENTS 4,944,297 A * 7/1990 Ratkoff ...................... A61F 7/00
                                                              607/96
5,451,747 A * 9/1995 Sullivan ..................... A61F 7/007
                                                             219/505
(Continued)

FOREIGN PATENT DOCUMENTS

EP          1231875 B1 *  9/2004  ............. A61F 7/007

*Primary Examiner* — Kaitlyn E Smith
*Assistant Examiner* — Bradford C. Blaise
(74) *Attorney, Agent, or Firm* — FisherBroyles, LLP; Robert Kinberg

(57) ABSTRACT

The invention relates to a device for hyperthermic treatment of itching, for example following insect bites, wherein during the treatment a treatment surface is regulated at a temperature of preferably between 42° C. and 56° C. for a period of 2 sec to 12 sec and a hardware-implemented temperature monitor limits the maximum temperature of the treatment surface and a safety fuse shuts off the device in the case of a short-circuit or uncontrolled continuous heating.

14 Claims, 1 Drawing Sheet

(52) U.S. Cl.
CPC ............... *A61F 2007/0095* (2013.01); *A61F 2007/0096* (2013.01); *A61F 2007/0284* (2013.01)

(56) References Cited

U.S. PATENT DOCUMENTS

| | | | | |
|---|---|---|---|---|
| 6,245,093 B1* | 6/2001 | Li | ............................ | A61F 7/007 607/96 |
| 2004/0127962 A1* | 7/2004 | Li | ............................ | A61F 7/007 607/96 |
| 2007/0049998 A1* | 3/2007 | Conrad | .................... | A61F 7/007 607/96 |
| 2010/0179623 A1* | 7/2010 | Hofer | ....................... | A61F 7/007 607/96 |
| 2011/0040235 A1* | 2/2011 | Castel | ........................ | A61F 7/00 604/20 |
| 2011/0049128 A1* | 3/2011 | Chow | ................. | G05D 23/1917 219/494 |
| 2011/0208268 A1* | 8/2011 | Brown | ................ | A61N 1/37254 607/60 |
| 2012/0065556 A1* | 3/2012 | Smith | ................. | A61H 23/0263 607/109 |
| 2012/0228279 A1* | 9/2012 | Haas | ......................... | H05B 1/02 219/211 |
| 2012/0257364 A1* | 10/2012 | Brooks | ................. | H05K 3/284 427/490 |
| 2012/0318781 A1* | 12/2012 | Lavin, Jr. | .............. | A41D 13/005 62/259.3 |
| 2014/0352325 A1* | 12/2014 | Brown | ................... | F25B 21/02 62/3.2 |
| 2014/0358200 A1* | 12/2014 | Ko | ......................... | A61N 1/328 607/101 |
| 2019/0290476 A1* | 9/2019 | Zippenfennig | ......... | A61P 43/00 |
| 2019/0290477 A1* | 9/2019 | Bunger | ................... | A61P 17/04 |

\* cited by examiner

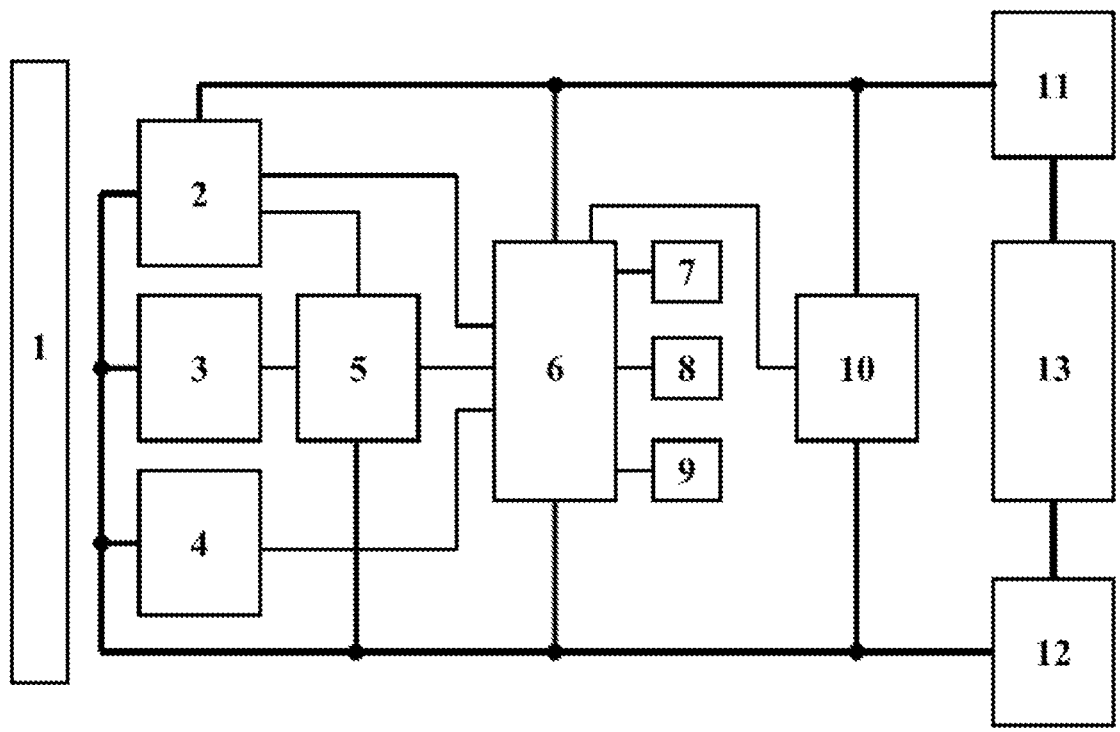

DEVICE FOR HYPERTHERMIA TREATMENT OF ITCHING

DESCRIPTION

The invention relates to a device for hyperthermic treatment of itching, for example following insect bites, wherein during the treatment a treatment surface is regulated at a temperature of preferably between 42° C. and 56° C. for a period of 2 sec to 12 sec and a hardware-implemented temperature controller limits the maximum temperature of the treatment surface and a fuse shuts off the device in the case of a short-circuit or uncontrolled continuous heating.

BACKGROUND AND PRIOR ART

Itching (pruritus) is a subjectively unpleasant sensory perception occurring on the skin or mucous membrane. It may be locally delimited or affect the entire body.

Frequently itching is accompanied by a burning, stinging or tinging sensation, which the affected person often tries to relieve by scratching, scraping, rubbing, pinching, kneading or chafing. Therefore itching often results in additional pathological skin manifestations such as scratches, open wounds, scabbing and skin infections. Experts assume that itching is mediated by pain receptors in the skin and conducted to the brain through the sympathetic nervous system. Itching may have many causes. In addition to dry skin, lack of moisture or allergies, itching may also arise due to external effects and skin irritations, e.g., mosquito bites or contact with nettles. Itching may be a reaction to chemical, mechanical or thermal stimuli. It may be caused by external irritation, e.g., contact with chemical substances, e.g., histamine (mosquito bite), apamine (bee sting), allergic immune reactions, pressure or friction or also heat or sun exposure, wheals, urticaria and other skin reactions associated with itching. From the medical viewpoint, the causes or underlying illnesses that result in itching cover a broad range of dermatologic and internal diseases.

A number of medications or cosmetic products are known for pharmaceutical treatment of the symptoms of itching. For example, essential oils especially comprising menthol, thymol or camphor are used to produce short-term cooling. In addition, skin care agents such as creams or lotions may have a pain-relieving effect by increasing the moisture content of the skin. Furthermore antihistamines represent helpful therapeutic options, for example comprising the administration of dimetindene maleate or mepyramine. Additional medications include topical glucocorticoids, anesthetics, zinc ointments, calcineurin inhibitors or capsaicin.

In addition, to treat wasp or bee stings, the sites of the stings may also be treated with spirits of ammonia, but this provides only brief relief of itching and also reduces the swelling only slightly.

However, it is also known from the prior art to reduce the development of itching by applying a quantity of heat to the site of the sting. A device for local thermal treatment especially of mosquito bites is described in EP 1231875 B1. The device has a hot plate about 0.2 cm$^2$ in size, which is brought to a temperature between 50° C. and 65° C. while the hot plate is in contact with the insect bite. The itching can be enduringly relieved by this hyperthermic treatment. On one hand, the application of heat causes the breakdown of the thermolabile insect toxins responsible for the itching. On the other hand the heat transfer results in masking of the itching by other temperature-related skin sensations. Thus as a result of such treatments, secondary injuries to the skin, for example inflammation of the insect bite due to scratching, may also be effectively avoided. In this way the hyperthermic treatment also effectively reduces the development of wheals accompanying an insect bite.

The possible applications of hyperthermic treatment also extend to herpetic diseases. From DE 102005002946 A1 a device is known for the treatment of herpetic diseases. The device comprises a hot plate with a preferred size of 20 mm$^2$, which is heated to 49° C.-53° C. for a treatment duration of preferably 10-15 sec. During the treatment period, the hot plate contacts the affected skin parts of the lips, for example the reddened areas or also the location at which blisters have already formed. The application of heat leads, on one hand, to suppression of the multiplication of the causative organisms by a neutralizing effect on the herpes simplex viruses. On the other hand, the brief treatment results in the masking of itching from the herpetic disease by the stimulation of temperature-sensitive nerves. The device is thus characterized by reduction of the symptoms of the herpetic disease, for example burning, development of swellings or redness, or itching.

In addition, from the prior art of US 2007/0049998 A1 an instrument that provides a treatment temperature of 50° C. is likewise known for hyperthermic treatment of insect bites. This instrument has the drawback that processes that relieve itching are not yet triggered or fully triggered at this temperature. Some of the processes essential for the hyperthermic treatment that contribute to alleviating the symptoms of insect bites, herpetic diseases, jellyfish stings or other diseases accompanied by itching are only activated in a temperature range between 50° C. and 56° C., especially between 50° C. and 53° C.

The devices for hyperthermic treatment known from the prior art are characterized by many possibilities for use in alleviating the symptoms of insect bites, herpetic diseases, jellyfish stings or other diseases accompanied by itching. However, the devices also have drawbacks.

For example, in the known devices, in exceptional instances the desired treatment temperature may be exceeded. However, it is also known from the prior art to control the treatment temperature using temperature sensors. Damage to the instrument, e.g., by contact with moisture, may result in impairment of the control circuit of the electronic control arrangement. This is especially the case if the control of the treatment temperature is incorporated into the regular control circuit. In this case the possibility cannot be ruled out that the temperature may be raised above the desired treatment temperature. Depending on the contact position of the hot plate or treatment surface, this will result in undesirable effects. Even a brief temperature increase above 65° C. can cause lasting injuries to the affected skin parts. This is especially the case for thermosensitive skin parts, for example the lips during herpes treatment or thin skin parts on which insect bites are present.

An instrument is known from US 2007/0049998 A1 for hyperthermic treatment of skin symptoms, which heats a treatment surface using a temperature-controlled heating element to temperatures of 38° C.-67° C. for a duration of at least 5 seconds, but typically for a longer time period, and uses a fuse for protection against overheating. This method of protection against overheating has the drawback that after being triggered by overheating, the fuse must be replaced. In addition no redundant safety mechanism is present, and if the fuse fails, overheating of the treatment surface for a prolonged period is threatened. Furthermore temperatures of 60° C. or above, especially over a period of several seconds or more, are felt as very unpleasant and can damage the skin. This can at least result in jeopardizing the success of treatment because treatments will be interrupted prematurely because of the unpleasant skin sensation caused by the high temperatures and thus the success of treatment jeopardized. The instrument is based on the therapeutic concept of using the application of heat to destroy bacteria and kill skin irritants. However, the treatment durations and/or temperatures are not suitable of lastingly relieving itching by targeted stimulation of certain receptors and modification of the immune system. On the other hand, temperatures below 42° C. are unsuitable for achieving therapeutic effects through a sensation of warmth.

US 2011/0184502 A1 describes a heating pad for various applications, some of them medical, which electrically creates temperatures of 38° C.-71° C. for at least several minutes. Non-resetting thermal fuses in series are suggested as a redundant safety feature. Thus to be sure a redundant safety mechanism is present, but this is not reversible and must be replaced after being triggered. A second drawback of the use of thermal fuses is that these only melt after a temperature above a threshold value is applied. Thus thermal fuses only react after a certain reaction time when this critical temperature is applied and thus perhaps too late compared with a safety fuse. A safety fuse already opens in the case of an electric current above a threshold value, which can cause an excessive temperature if it flows for too long a time. In addition, both the temperature range and the duration of the heating process are surely relevant for a number of applications, but are unsuitable for lastingly alleviating pruritus through application of heat.

Thus it would be desirable to be able to supply a device which implements the advantages of hyperthermic treatment and simultaneously minimizes safety risks, preferably by using a redundant safety mechanism against overheating but one that is also practical and meets high standards.

Problem of the Invention

Thus one problem of the invention would be to supply a device for hyperthermic treatment that eliminates the drawbacks of the prior art. Thus one problem of the invention would be to supply a device for hyperthermic treatment that eliminates the drawbacks of the prior art.

SUMMARY OF THE INVENTION

The task is accomplished according to the invention with a device according to the independent claims. The dependent claims present preferred embodiments of the invention.

In a preferred embodiment, the invention relates to a device for hyperthermic treatment of itching comprising a) at least one treatment surface and b) a control device for regulating the temperature of the treatment surface, wherein the control device can regulate the treatment surface by heating at least one heating element in a heating phase to a treatment temperature of between 42° C. and 56° C. and in a treatment phase the treatment temperature can be held for a period of 2 to 12 sec, wherein a hardware-implemented temperature controller limits the maximum temperature of the treatment surface at a value of between 54° C. and 58° C., preferably approximately 56° C., and a fuse shuts off the power supply to the device in case of a short-circuit or uncontrolled continuous heating.

The term "hyperthermic treatment of itching" in the sense of the invention is preferably defined as treatment of illnesses which are generally accompanied by the occurrence of itching. As was previously mentioned, this especially comprises the treatment of itching that may occur after an insect sting or contact with poisonous cnidarians or plants. In addition, a preferred application of the device for the hyperthermic treatment of itching is the treatment of herpetic diseases or other skin irritations that cause redness, swelling or other unpleasant symptoms that accompany itching. Itching can be caused by parasites as well as by a mechanical or chemical (e.g., environmental toxins or medications) exposure, preferably of the skin. However, skin itching may also be caused by eating a certain food, endoparasites, as well as autoimmune reactions, skin fungi, allergies, xeroderma, senile itching, winter itching, kidney or liver diseases, metabolic disorders, tumors, temperature fluctuations, water contact or psychological disturbance. To relieve the symptoms of these various diseases, especially the itching, the device according to the invention is preferably placed on the affected skin parts. After contact of the skin part with the treatment surface, a control device ensures that regulation of the temperature of the treatment surface according to the invention takes place. Preferably for this purpose, the treatment surface is first brought during a heating phase to a treatment temperature of between 42° C. and 56° C. It is preferred for the treatment phase not to take a long time. Preferably the heating phase should take no more than 10 sec, particularly preferably no more than 3 sec. Following the heating phase, the temperature of the treatment surface is preferably held at the predetermined treatment temperature. Preferably for this purpose, the treatment temperature is a constant temperature falling in the range mentioned, between 42° C. and 56° C.

This treatment temperature is preferably kept constant during the treatment phase. However, it may also be preferred for the treatment temperature not to be kept constant. For example, the treatment surface can also be brought in a temperature ramp to a maximum temperature in the range of the treatment temperature between 42° C. and 56°. Thereafter it may be preferred for the temperature to be brought briefly below the range of the treatment temperature. Then the temperature can rise again in a ramp. This preferred variant has surprisingly been found to be advantageous over maintaining a constant treatment temperature in the case of some skin diseases leading to itching. For example it may be advantageous to reach the maximum temperature only for a very brief time over an increasing temperature, and then to cool again somewhat via a ramp.

The treatment phase preferably designates the time period during which the temperature is in the range of the treatment temperature of 42° C. to 56°. Particularly preferably the treatment phase lasts between 2 sec and 12 sec, most particularly preferably between 3 sec and 6 sec. It is particularly preferred for the treatment phase to represent a continuous time period. However, it is also possible for the treatment phase to be briefly interrupted by controlling the temperature in a ramp. In this case the period of the treatment phase preferably designates the time period during which the temperature of the treatment surface is in the range of the treatment temperature of 42° C. to 56° C.

By regulating the treatment surface to a temperature of between 42° C. and 56° C. for a treatment phase of between 2 sec and 12 sec, preferably between 4 sec and 6 sec, a heat pulse is generated which makes it possible to apply a well-defined quantity of heat to the skin area in a controlled manner. In this way advantageously e.g., the itching that occurs due to an insect sting, for example by a wasp or bee, can be effectively relieved with surprising speed. On one hand, the application of heat causes the breakdown of the thermolabile insect toxins responsible for the itching. On the other hand, the heat pulse causes nerve stimulation, which greatly reduces the subjective perception of itching at the affected sites. Surprisingly, the heat transfer results in masking of the itching by other temperature-related skin sensations. Unlike conventional methods for treating pruritus, which target the itching sensation by regulating the pain receptors, the preferred heat treatment activates the free nerve endings of the C fibers. The C fibers in particular refer to the slowly conducting nerve fibers of the somatosensory system and are responsible for the sensation of pain. In this process in particular the free ends of the C fibers, which are also called nociceptors, play an important role. The nerve endings of the fibers are activated by tissue hormones (e.g., histamine, serotonin, substance P). In addition, mast cells in the vicinity of the nerve endings can become involved in the process by releasing the mediator tryptase. In particular, knowledge of the action mechanism in pruritus is used to regulate the sensory perception triggered by the fibers in a surprising manner by heat treatment. In addition to the particularly preferred use of the device for treating itching in the case of insect stings, the time periods and temperature values enable the treatment of herpetic diseases, and surprisingly also other itching disorders, e.g., after contact with poisonous cnidaria or plants such as stinging nettles.

A preferred variant uses a treatment temperature of between 42° C. and 56° C. and particularly preferably between 50° C. and 53° C. Very surprisingly it has been found that itching can be especially greatly reduced with the above-named parameters. A treatment temperature of between 42° C. and 56° C. and especially the preferred treatment temperature between 50° C. and 53° C. has an effect on the skin parts which relieves itching quickly and effectively. In particular it has been recognized that an especially pronounced masking of the itching sensation can be attained if the thermal and capsaicin receptors, TRPV1 and TRPV2, are simultaneous activated locally in the affected skin parts.

TRPV1 is involved in acute heat-induced pain in healthy skin and regulates, for example, the sensation of heat at temperatures at 45° to 50° C. In addition, TRPV2 is activated in the case of especially strong painful heat sensations that occur at temperatures above 52° C. The activation threshold of TRPV1 is between 40° C. and 45° C., whereas that of TRPV2 is between 50° C. and 53° (Yao et al 2011, Somogyi et al. 2015, Cohen et al. 2014, Mergler et al. 2014).

Whereas an initial understanding of the mode of action of TRPV1 and TRPV2 receptors as temperature sensors has emerged from recently published research findings in the literature, their role in the perception of itching is unknown. Therefore a person skilled in the art, even knowing the literature, would not assume that specifically the activation of these receptors would allow particularly effective masking of the itching sensation. This is a surprising observation, which is utilized especially in the particularly preferred embodiment mentioned, which provides for temperature regulation of the treatment surface in a narrow range of between 50° C. and 53° C. Temperature regulation of the treatment surface in a narrow range of between 50° C. and 53° C. enables in a surprisingly effective manner simultaneous activation of the receptors without causing unpleasantly intense pain sensations in the people being treated. It was possible to determine experimentally the range of the activation threshold of TRPV2 as an especially optimized operating range. In this range it is assumed that a feedback mechanism develops between the receptors, which especially effectively masks the itching without causing side effects. The preferred treatment of the skin parts leads to alleviation of the itching sensation, which surprisingly still lasts for hours after treatment. The long-lasting mode of action of the preferred embodiment is at least partly attributable to immune regulation by the heat transfer. Thus not only is the pain sensation masked, but the local skin irritation is actively suppressed by regulation of the immune system. Advantageously, therefore, a single treatment can already lead to persistent relief from the itching sensation. However, it may also be preferred for treatment to be performed several times in chronological sequence. The interval-like transfer of the heat with a treatment phase of 2 sec-12 sec or particularly preferably 4 sec to 6 sec achieves an optimal effect on the signal pathway of the itching without causing adverse effects.

In the meaning of the invention, the treatment surface preferably designates the area of the device which is heated to the treatment temperature during treating and is in direct thermal contact with the skin part. The treatment surface can be a continuous surface area. However, it may also be preferred for the treatment surface to consist of several noncontiguous partial areas. The size of the treatment surface preferably depends on the disease and the size of the skin parts affected by the symptoms of the itching disorder. In the case of insect bites the size of the treatment surface is between 10 mm$^2$ and 100 mm$^2$, particularly preferably between 20 mm$^2$ and 60 mm$^2$. In the treatment of herpes, the treatment surface is preferably between 10 mm$^2$ and 80 mm$^2$, particularly preferably between 20 mm$^2$ and 50 mm$^2$. In addition i is particularly preferred that the treatment surface for these small skin parts is circular. As a result of the sizes and geometries of the treatment surface selected in this way, a treatment optimally adapted to the cause can take place, which optimizes efficiency and well-being and thus contributes to longer-lasting success of treatment. For the treatment of large-area skin diseases accompanied by itching, for example after contact with poisonous jellyfish, treatment surfaces of 1 cm$^2$ to 18 cm$^2$, preferably between 6 cm$^2$ and 9 cm$^2$, may be preferred. Up to now experts have assumed that in the case of skin parts involved in large-area treatment, positive relief of itching might be masked by strong negative adverse effects such as burning of the skin or hyperthermic pain sensations. However, it was recognized that with a larger treatment surface of about cm$^2$ to 18 cm$^2$, preferably between 6 cm$^2$ and 9 cm$^2$, surprisingly large-area skin parts affected by pruritus may also be treated. For example, it is possible in the case of skin eruptions, by conveniently and simply applying the treatment surface to the corresponding skin parts, for the itching sensation to be converted to a tolerable pain sensation by masking with heat. Secondary injuries to the skin, for example formation of wounds due to scratching, may be effectively avoided in this way. With devices having smaller treatment surfaces, multiple application at different positions would be necessary for treating large-area skin parts. However, the same effect cannot be achieved with this because of the progression of time.

It may also be preferred to use a treatment surface between 7 cm$^2$ and 18 cm$^2$. External stimuli, chemical, mechanical or physical in nature, that can trigger itching sensations are perceived by three different receptor cells (sensory cells). These sensory cells are so-called open nerve endings, the stimulus-receiving structures of which are located in the epidermis and the underlying dermis, and the axons of which conduct the signals about stimuli perceived into the spinal cord. In these sensory cells the nonmyelinated C fibers are of particular significance. The receptive structures thereof are in some instances 0.1 mm below the skin surface. In the case of the C fibers, a distinction is made between polymodal mechanical and heat-sensitive fibers and mechanically insensitive C fibers, but which can also be stimulated by heat. C fibers not only detect pruritogenic stimuli, but also serve as nociceptors (pain receptors). It was shown in the literature that heat stimuli, as counterirritants, can suppress itching sensations. The individual C fibers perceive stimuli from a certain area of the skin, wherein a defined skin area is innervated by a sensory cell. This region is designated as a receptive field. The receptive fields of C fibers can also be overlapping. Studies in humans using so-called micro-mapping have shown that the mechanically insensitive C fibers have fields of up to 5 $cm^2$ in size; those of mechanically sensitive C fibers are somewhat smaller and up to 2 $cm^2$ in size. In the preferred treatment size between 7 $cm^2$ and 18 $cm^2$ therefore the receptive fields of the different C fiber types are surprisingly masked and in addition the effect of the horizontally outflowing heat is compensated.

The size of the treatment surface is preferably related in each case to the total contact area over which a skin part is subjected to a heat pulse. In the case of a treatment surface consisting of several partial areas, the size of the treatment surface preferably corresponds to the total of the individual partial areas. In certain manifestation forms of itching-inducing illnesses, such a division into partial areas can be advantageous, as in the treatment of certain body sites.

It is preferred that the treatment surface be brought to the treatment temperature with the aid of at least one heating element. In a preferred embodiment, the treatment surface corresponds to the surface area of a hot plate heated using a heating element, wherein for example a semiconductor component can be used. However, the treatment surface may also designate a homogeneous material surface that is temperature-controlled by several heating elements. For example, it may be preferred to use two or four heating elements to bring the treatment surface especially homogeneously and rapidly to the treatment temperature. It may also be preferred to coat a hot plate comprising a heating element. In this case, the treatment surface is preferably defined as the coating on the hot plate. Thus the treatment temperature preferably always specifies the temperature present at the skin part of the patient. Through the embodiment relating to the combination of heating element and treatment surface preferred depending on the area of use, a device optimized in terms of efficiency, compactness and success of treatment may be provided.

It is preferred that the control device can regulate the heating of the heating element in such a way that the treatment temperature is present at the treatment surface. In this way, optimal control of the treatment temperature can be guaranteed and undesirable overheating of the treatment surface can be prevented.

According to the invention, the control device is preferably a processor, a processor chip, microprocessor or a microcontroller that is configures to regulate the temperature of the treatment surface with the aid of the at least one heating element according to the pre-specified values for the treatment temperature. Such a control device is characterized by compactness, reliability, cost-efficiency, low power consumption and high control efficiency.

The at least one heating element is a component for which various embodiments from the prior art are adequately known. For example, the heating element may comprise a power resistor in which a well-defined temperature is generated, depending on the current flow. Preferably a field effect transistor (FET) can be used for quantitatively controlling the flow of current through the heating element. However, it may also be preferred to use an FET itself as a heating element. Here, energy dissipation in the transistor itself is used to generate heat and to bring the treatment surface to the treatment temperature. FETs are particularly preferred as heating elements, since they allow a low size of the device because of their small dimensions. In addition, FETs are especially reactive and guarantee, through highly dynamic heat generation and heat release, particularly rapid response behavior of the heating elements.

Preferably the control device, by presetting the current feed to the heating element, can control the temperature present at the treatment surface. For example, using a calibration, the correlation between current flow and/or voltage at the heating element and the temperature at the treatment surface can be determined, so that based on this calibration a desired treatment temperature between 42° C. and 56° C. can always be set. However, it may also be preferred to regulate the treatment temperature by means of the control device using a feedback loop. Thus it may be preferred to use a temperature sensor that measures the temperature of the treatment surface, wherein the control device regulates the current feed to the heating element based on the temperature data. For this purpose, for example the control device may comprise a microprocessor that can evaluate measurement data and establish current parameters. In this way the temperature can be controlled very efficiently and reliably.

Particularly preferably the device comprises at least two additional safety elements that control the temperature of the treatment surface.

On one hand the device comprises a hardware-implemented temperature controller, which limits the maximum temperature of the treatment surface to a value of between 54° C. and 58° C., preferably approximately 56° C. The maximum temperature preferably designates the maximum temperature that the treatment surface reaches during the treatment phase. The hardware-implemented temperature controller advantageously makes it possible to ensure that the maximum temperature does not exceed a value of between 54° C. and 58° C., preferably approximately 56° C. In the meaning of the invention, statements such as about, approximately, nearly or synonymous concepts preferably designate a tolerance range of less than ±10%, preferably less than ±5% and particularly preferably less than ±1%. In the meaning of the invention, a "hardware-implemented temperature controller" preferably designates a temperature control system for the treatment surface which is hardware-based and can switch off the power supply to the heating elements for the treatment surface. In particular, the "hardware-implemented temperature controller" preferably allows for switching off the power supply to the heating elements when the maximum temperature is exceeded, independently of the regulation of the heating element by the control device, thus for example the microprocessor. For example, if a firmware program for regulating the heating elements is already installed on the control device, it is preferred for the hardware-implemented temperature controller to also reliably limit the maximum temperature of the treatment surface even in case of failure or incorrect performance of the firmware.

In this way it is possible to ensure especially effectively through simple design means that the treatment surface of the device does not exceed a maximum temperature. Even if controlling errors occur in the control device, for example after liquids get in, because of the hardware-based temperature controller it is possible advantageously at any time to ensure that treatment surface does not exceed a maximum temperature of a value between 54° C. and 58° C., preferably approximately 56° C. Through this additional technical element for temperature control it is possible to guarantee an excellent safety standard without interfering with the functioning of the device for hyperthermic treatment.

Surprisingly it was found that a maximum temperature at a value of between 54° C. and 58° C., preferably approximately 56° C., does not jeopardize the success of treatment or produce an unpleasant sensation on the skin, so that this maximum temperature represents an ideal first safety step for preventing overheating.

As an additional safety element the device according to the invention has a safety fuse which, in the case of a short-circuit in the device or uncontrolled continuous heating of the device, interrupts the power supply to the device. In the meaning according to the invention, a safety fuse is preferably defined as an excessive current protective mechanism in which an electrical circuit can be interrupted, for example by the melting of a fuse element as soon as the strength of the current exceeds a limiting value for a time to be determined. It is preferred for the safety fuse to be located in the device between the input of the supply voltage into the device and the device itself. If a malfunction should occur that is characterize by the flow of an uncontrolled high current from the supply voltage feed into the device, the safety fuse will advantageously shut down the power supply to the device completely. A safety fuse offers sufficiently fast protection, and on the other hand, extremely reliable protection.

It has been found that even with faultless design of the device and the supplying of a hardware-implemented temperature controller it is not possible to rule out the occurrence of continuous heating of the heating elements in extremely rare instances because of incorrect operation. Continuous heating of the heating elements in the meaning of the invention preferably means that the temperature of the heating element rises uncontrolled, i.e., without temperature-based regulation with the aid of the control device. If during such breakdowns the hardware-implemented temperature controller fails, the treatment surface can rise uncontrollably to temperatures far above the desired treatment temperature, for example to temperatures far in excess of 65° C.

Although such undesirable continuous heating occurs extremely rarely, it can cause severe injuries to the patient. This is especially due to the fact that the skin parts to be treated with hyperthermia are usually particularly sensitive and, for example, are characterized by redness, swelling or even wound formation. A temperature distinctly elevated above 65° can lead to severe local pain at these sites and can cause burns to the skin.

In view of the special circumstances of use of the device and the associated safety requirements, the safety fuse mentioned is especially advantageous for being able to guarantee that the heating of the treatment surface will be switched off even in the most unlikely instance of a malfunction. For example with the aid of the safety fuse, independently of any temperature measurement, excessive heating of the treatment surface, due for example to defective temperature sensors, can be suppressed. It was recognized that the power supply to the device represents a central regulatory interface that meets the highest safety requirements. By integration of the safety fuse into the current flow for supplying the device it is possible to ensure that a maximum supply current will not be exceeded for a certain time. Since continuous heating and uncontrolled heating of the heating elements above the desired temperature are related to increased current flow, in this way overheating of the treatment surface can be avoided especially reliably. In particular, the current controller can react very quickly before the current is present for long enough that it will produce a temperature corresponding to its strength. A last-resort safety mechanism based purely on the temperature also might not be fast enough because of thermal inertia of the components involved.

In the device according to the invention, a particularly advantageous and synergistic effect of the combined use of a hardware-implemented temperature and a safety fuse is seen.

For example, one drawback of the safety fuse is that following the single triggering, permanent decoupling of the supply voltage from the device results. Resumption of the use of the device following triggering of the safety fuse requires repair by a technician, for example replacement of the safety fuse. From the viewpoint of expenses, the device is generally made unusable by triggering of the safety fuse.

Advantageously, however, the hardware-implemented temperature controller is set such that it need not cause permanent shutoff of the power supply to the device. Instead, the hardware-implemented temperature controller is designed such that when the temperature of the treatment surface exceeds a maximum temperature, the power supply to the heating elements is interrupted during the time of the exceedance. Thus the current interruption by the hardware-implemented temperature controller is advantageously reversible, i.e., as soon as the temperature of the treatment surface again drops below the maximum temperature, the heating elements can heat again.

Thus even after a one-time occurrence of a malfunction the normal use of the device can be continued. The user would also not notice the malfunction, since as a result of the maximum temperature selection, the effectiveness and the independence of the temperature controller, no temperatures perceived by the user as unpleasant will develop and once a malfunction has occurred, the device can function perfectly again upon the next use.

The combination of the safety features of a hardware-implemented temperature controller with a safety fuse allows for surprisingly reliable control of the temperature by the most economical means possible because of the hierarchy of safety barriers.

An additional synergistic effect due to the combination of the safety features of a hardware-implemented temperature controller with a safety fuse can be seen in the fact that for example an unlikely but possible one-time failure of the control device is reversibly held off by the hardware-implemented temperature controller. If, however, an extremely unlikely larger problem should occur, which comprises the hardware-implemented temperature controller, the safety fuse enters into action as a last resort. However, since this is irreversible, no further use by the user, which under these circumstances would be hazardous, can take place, but a trip to the technician or specialty shop is scheduled.

Preferably the temperature of the treatment surface is already taking place with the aid of the control device. If the control device fails due to, for example, faulty electronics, the hardware-implemented temperature controller will allow the heating elements to be shut off independently of the control device. Even in the case of such a malfunction of the control device, a safety fuse would not be triggered. Only in the extremely rare case that both the control device and the hardware-implemented temperature controller should fail, for example in the case of damage to the corresponding structural element, does the safety fuse guarantee a final control element. If an increased current demand for the heating elements occurs because of high heating, the safety fuse will shut down the power supply to the device completely. Through this gradation of the safety mechanisms a one-time malfunction of the control device can be headed off extremely safely. The hardware-implemented temperature controller intervenes unnoticeably and rapidly without influencing the usability of the device. An even higher safety level can be achieved with the downstream safety fuse, so that the user can be provided with an commonly effective and safe treatment device.

Surprisingly, by connecting the safety barriers in succession it is possible to guarantee that the treatment surface does not enter a temperature range that could put the patient in danger.

In a preferred embodiment of the invention, the device comprises at least one first temperature sensor for measuring the temperature of the treatment surface, in which the control device adjusts the temperature of the at least one heating element based on the measurement data of the temperature sensor. With such a temperature sensor, the temperature of the treatment surface can be regulated very reliably by the control device.

In the meaning of the invention, a temperature sensor is preferably an electrical or an electronic control element generates an electrical signal depending on the temperature. Many temperature sensors are known from the prior art, for example semiconductor temperature sensors, resistance temperature sensors, pyroelectric materials, thermocouples or vibratory quartz. The control device is also preferably configured such that this can receive and evaluate the measured values from the temperature sensors to effectuate regulation of the hot plates. The regulation of the heating plates can preferably be accomplished by applying an electric current or voltage. It is particularly preferred for the temperature sensor to measure the temperature of the treatment surface directly, i.e., for the temperature sensor to be in contact with the treatment surface, wherein the temperature sensor may be present on both the internal side of the treatment surface and the external side of the treatment surface or be implemented within the treatment surface. However, it may also be preferred that the temperature sensor does not directly contact and monitor the treatment surface, but instead, the heating elements or a material point between the heating elements and the treatment surface. In the case of several heating elements that heat the treatment surface, for example, it may also be preferred to place the temperature sensor between the heating elements. Likewise, a conclusion may be drawn regarding the temperature of the treatment surface from the measurement data for the temperature over the heating elements or a measurement site at a certain distance from the treatment surface. In the meaning of the invention it is preferred that the temperature of the treatment surface means the mean temperature of the treatment surface.

Evaluation of the temperature of the treatment surface allows particularly precise regulation of the at least one heating element to ensure an optimal temperature distribution on the treatment surface and thus heat transfer to the skin parts to be treated. Especially in view of the many application possibilities of the device for treating various diseases that may be accompanied by itching, a temperature-based feedback regulation with the aid of the control device is suitable for performing reliable hyperthermic treatment with optimal temperature values.

In a preferred embodiment of the invention, the hardware-implemented temperature controller comprises at least one second temperature sensor for measuring the temperature of the treatment surface and a comparator, wherein the comparator compares the temperature of the treatment surface with the maximum temperature, and if the maximum temperature is exceeded, stops the current feed to the at least one heating element. In the meaning of the invention, a comparator preferably designates an electronic circuit for comparing two voltages, wherein at the outlet it is shown in a binary comparison which of the two voltages is higher. In the prior art, various comparators are sufficiently well known, which are suitable for using two analog voltages to output one binary output signal, indicating which of the input voltages is higher. The Schmitt trigger may be mentioned as an example of a comparator circuit. It is preferred for a reference value for a voltage be applied to one input of the comparator using a voltage splitter. This reference value preferably corresponds to the voltage value that the second temperature sensor would show if the temperature of the treatment surface is equal to the maximum temperature. At the second input of the comparator, the output voltage of the temperature sensor, which depends on the temperature of the treatment surface, is preferably present. A particularly preferred temperature sensor has an NTC thermistor, i.e., a thermal resistor. This has a negative temperature coefficient, so that when the temperature increases, the resistance decreases and a higher current flows. However, posistors, i.e., PTC thermistors, having a positive temperature coefficient, may also be used, so that when the temperature increases, the resistance increases and a lower current flows.

If the temperature of the treatment surface rises, the voltage value at the comparator, regulated by the second temperature sensor, moves toward the voltage reference value that corresponds to the maximum temperature. As soon as the temperature exceeds the maximum temperature, the output signal on the comparator changes in a binary manner. The comparator is preferably integrated in the power supply of the heating elements. In other words, before the temperature of the treatment surface reaches the maximum temperature, the comparator preferably unblocks the supply voltage of the heating elements. However, as soon as the temperature is higher than the maximum temperature, the outlet of the comparator shuts off and interrupts the power supply to the heating elements. When the temperature of the treatment surface drops again, supply voltage is advantageously unblocked again by the comparator. As a result, reversible on and off switching of the heating elements can only take place for the time period during which the temperature of the treatment surface exceeds the maximum temperature. In addition it may be preferred for the comparator to be unlocked by the control device when the device is turned on. Thus if correct start-up of the device does not take place, the comparator is configured in the setup phase such that the current feed of the heating elements is interrupted.

The preferred embodiment of the hardware-implemented temperature controller described has proven in tests to be especially robust and reliable. Because of the reversibility of the safety switch and the simple design, the preferred embodiment is also characterized by low manufacturing and maintenance costs.

Due to the design independent of the control device and to the dedicated temperature sensor, reliable operation can be guaranteed even in the case of failure of a component of the control device.

In addition, a hardware-implemented temperature controller in the described form using a comparator is especially rapid, since comparators are widely used electronic components which are distinguished by their reliability as well as their rapid switching capacity. Thus for example, comparators with switching times of a nanosecond or less are available. Surprisingly it was found that through the use of comparators in the circuit, because of their high action speed, a particularly effective mechanism for protection from overheating of the treatment surface could be constructed.

In a preferred embodiment of the invention, the device is characterized in that the safety fuse has a threshold value for a maximum current which corresponds to the heating of the treatment surface to a value of between 65° C. and 70° C., preferably of 65° C. for 1 second. Tests have shown that only a temperature increase to above 65° C. for more than 1 second is highly critical for the pain sensation and can cause damage to skin parts. Advantageously, by setting the safety fuse for these parameter values, the safety fuse will not be triggered prematurely in the case of noncritical temperature elevations of the treatment surface. In this way it is possible to increase the economic efficiency without compromising on safety. The person skilled in the art knows, based on the electrical parameters of the heating elements, which safety fuse should be selected to guarantee the indicated values. For this purpose, the current flow may be measured while simultaneously measuring the temperature of the treatment surface. In addition it is particularly preferred to use a fast-acting safety fuse, which preferably reacts to a current increase within less than 20 ms. Thus it was recognized that even a short-term increase in the current for less than 20 ms can lead to a temperature elevation for more than 1 second because of the thermal inertia of the treatment surface.

Compared with non-resettable, purely temperature-dependent thermal fuses, which likewise function by melting, the current-dependent safety fuse used here has several advantages. In the case of non-resettable, purely temperature-dependent thermal fuses, the melting does not take place upon application of a current above a threshold value, but only upon application of an external temperature that is higher than a defined maximum temperature. Thus in contrast to non-resettable, purely temperature-dependent thermal fuses, current-dependent safety fuses can react even before a certain undesirable temperature is reached as a result of an elevated current acting for a relatively long period. Likewise, non-resettable, purely temperature-dependent thermal fuses always require a certain reaction time in the presence of an external temperature above a defined maximum temperature. In this way, dangerous further temperature elevations can occur. In contrast to this, current-dependent safety fuses react more quickly and with minimal system-related latency times.

In a preferred embodiment of the invention, the device is characterized in that the threshold value of the safety fuse is preferably between 1 A and 2.5 A, particularly preferably about 2 A. Tests have shown that with regard to the preferred heating elements, the threshold values mentioned guarantee with especially good reliability that the temperature of the treatment surface will exceed a temperature of 65° C. to 70° C. for no more than 1 second. Thus it is possible to ensure by the melting of the safety fuse above 1 A to 2.5 A that the temperature of the treatment surface cannot enter a range that is hazardous to health. Thus in the case of a normal treatment, a normal treatment current that is less than 2.5 A, preferably 1 A. If a malfunction occurs, e.g., in case of continuous heating, an increased current will flow. In this case, the fuse intervenes and effectively prevents uncontrolled heating.

Through the advantageous selection of the maximum temperature of the hardware-implemented temperature controller at a value between approximately 54° C. and 58° C., preferably at approximately 56° C., it is also possible to make sure that the distance from the temperature for triggering of the safety fuse by a current value above the threshold value is large enough. For example, unintended triggering of the safety fuse, which would result in at least the replacement of the fuse, can be avoided as long as no serious malfunction, including the hardware-implemented temperature controller, is present.

In a preferred embodiment of the invention, the device is characterized in that the treatment surface has a thickness of between 0.2 mm and 5 mm, preferably between 0.5 mm and 2 mm, particularly preferably between 1 mm and 1.5 mm, and consists of a material having a thermal conductivity at 50° C. of between 20 W/mK and 400 W/mK, preferably between 100 and 350 W/mK. The thermal conductivity (also known as the heat transfer coefficient) preferably characterizes the thermal properties of the material from which the treatment surface is made. The thermal conductivity indicates the quantity of heat conducted through the treatment surface when a temperature gradient is applied to it. In addition to the thermal conductivity, the heat transport depends on the thickness of the treatment surface, the size of the treatment surface and the temperature difference between the inside of the treatment surface (contact with the heating elements) and the outside of the treatment surface (contact with the skin). The thermal conductivity is preferably reported as the ratio of the transported heat output in watts (W) per unit temperature difference in kelvin (K) and per meter (m). However, the thermal conductivity can also be preferably reported as the ratio of the transported heat output in watts (W) per unit temperature difference in millikelvin (mK). Since the thermal conductivity can also change slightly as a function of the temperature, in the present case the reference temperature is given as 50° C. The thickness of the treatment surface also preferentially designates the size of the treatment area between the outermost surface that contacts the skin and the innermost surface to which the heating elements are applied.

At a treatment surface thickness of between 0.2 mm and 5 mm, preferably between 0.5 mm and 2 mm and particularly preferably between 1 mm and 1.5 mm, in combination with the preferred thermal conductivity at 50° C. of between 100 and 350 W/mK, a particularly therapeutically effective release of heat to the skin takes place. Under experimental conditions the preferred parameters mentioned proved surprisingly advantageous. For example, a treatment surface designed in this way avoids excessively rapid release of the heat to the affected skin parts, which could cause unpleasant stabbing pain. Nevertheless the heat release takes place during a time period that is sufficiently abrupt to effectively activate the receptors and mask itching. Therefore the parameters mentioned represent an optimized selection that was not obvious for the person skilled in the art. In addition, the parameters preferably guarantee that during the treatment phase, the heat from the treatment surface will be released rapidly and effectively to the skin parts, so that emergence of residual heat will not represent a risk.

In a preferred embodiment the treatment surface comprises ceramic or gold. It is particularly preferred for the treatment surface to consist of gold or ceramic. The materials ceramic and gold on one hand fall within the experimentally determined preferred thermal conductivity range. In addition, the materials themselves preferably do not store heat for too long, so that these materials heat and cool again relatively rapidly. This allows increased safety, since it is possible to ensure that after the treatment phase, the heat from the treatment surface will not represent a risk due to residual heat. In addition, both ceramic and gold are characterized by high biological compatibility at the preferred treatment temperatures. Allergic reactions or other adverse effects can be especially effectively avoided when these materials are selected.

In a preferred embodiment of the invention, the device is characterized in that the treatment area is surrounded by a marker that lights up depending on the treatment cycle. For example, as a marker it may be advantageous to surround the treatment surface with a light guide. This can be illuminated, for example, during the heating phase or during the treatment phase. It has been found that the success of the hyperthermic treatment can be increased by using an explicit, glowing indication of the position of the treatment surface.

For example, the visual marking promotes centered application to the affected skin parts, so that the heat pulse can be applied to these skin parts in a targeted manner. With the illuminated marker, the device can also be used in the dark, for example in a tent outdoors at night, without problems.

In an additional preferred embodiment of the invention, the device is characterized in that the device comprises an optical display or sound generator that indicates the start of the heating phase, the reaching of the treatment temperature, the duration of the treatment phase and/or the end of the treatment phase with an acoustic or optical signal. The optical display can preferably take place by means of light-emitting diodes (LED), light bulbs, liquid crystal (LCD) displays or other known optical display types. Preferably a color code adapted to the function is used. For example, the heating phase can be indicated by an orange signal, the treatment phase by a red signal and the end of the treatment phase by a green signal. The acoustic signal generation is preferably accomplished by a loudspeaker, which preferably emits short or longer beeping sounds. Through the optical and/or acoustical signaling, the user learns the status of the device at any point in the preparation or treatment phase. Surprisingly this causes an additional psychological effect, which leads to an even greater reduction in itching through concentration on the signal generated. In addition, with the preferred embodiment, the ease and safety of operation as well as patient compliance are greatly increased. Furthermore the optical and/or acoustical signaling makes it possible to introduce additional safety mechanisms. For example, the user can be rapidly and clearly informed that the temperature has exceeded the maximum allowed. Consequently the user can remove the treatment surface from the skin part before skin damage can occur. It has been found that the self-protective reaction to pain sensations is distinctly slower than the reaction to an optical and/or acoustic warning signal, so that the signal generation represents an additional, effective safety feature of the device.

In an additional preferred embodiment the device comprises a watertight housing. The housing is preferably an external casing for the device that particularly surrounds the control device and other electronic components. It is preferred for the housing to have a housing head and a housing handle, wherein the treatment surface is preferably located on a lower section of the housing head. For controlling and managing the temperature of the treatment surface, the housing preferably has a cutout at the appropriate position. In the preferred embodiment the housing is designed such that all cutouts, e.g., also any battery compartments that may be present, are watertight. For example, seals or suitable gaskets, possibly made of elastomers, may be used for this purpose. However, the person skilled in the art is familiar with numerous other technical possibilities for designing a watertight housing. The watertight design of the housing represents an additional safety element, since in this way damage to the control device or other electronic components due to infiltrating liquids can be effectively avoided. In addition, the watertight housing results in the avoidance of corrosion and thus to an extended useful life of the device.

In particular, the invention in this preferred embodiment in combination with the illuminated marker is also suitable for use under special conditions, for example on expeditions in areas remote from civilization, in sometimes hot, moist climates.

In another preferred embodiment of the invention, the device is characterized in that the device comprises a power supply unit as well as a voltage controller that monitors the voltage of the power supply unit. In the meaning of the invention, the power supply unit preferably provides the electrical energy for operating the device. Preferred power supply units are regular batteries or rechargeable batteries. These usually supply the electrical energy by providing direct current. In the preferred embodiment, the voltage supplied by the power supply unit is monitored using a voltage controller. In the meaning of the invention, a voltage controller is preferably an electrical switch which can measure the voltage of the power supply unit and trigger an action if this falls below a predetermined limit value. In the prior art, a number of variants for voltage controllers are known, wherein the person skilled in the art knows which voltage controller is suitable for which types of power supply units, i.e., especially for regular batteries or rechargeable batteries. It is preferred that if the voltage controller detects a drop in the voltage of the power supply unit below a certain value, it will transmit an interrupt request (IRQ) to the control device, which is preferably a microprocessor. If a treatment cycle, i.e., a heating phase or a treatment phase, is in operation during this time, the interrupt request will lead to termination of the treatment cycle. This is an additional safety mechanism. Thus it was found that an insufficient voltage on the power supply unit can cause failure of the control device, e.g., the microprocessor. In this case it may occur that the temperature regulation of the treatment temperature will not be performed correctly with the control device and uncontrolled heating of the treatment surface will occur. Thus the voltage controller can also contribute to increasing the safety of the device and avoiding a health risk, for example in the case of a defective battery.

In a preferred embodiment, the device is characterized in that the control device comprises a microprocessor. In the meaning of the invention, a microprocessor is preferably a data processing device, i.e., a processor, which is characterized by small dimensions, in the range of several mm, and wherein preferably all building blocks of the processor are located on a microchip or an integrated circuit (integrated circuit, IC). Preferably the microprocessor can also be a microcontroller, which in addition to the processor integrates additional peripheral elements on the microchip and for example also has a data memory. It is also preferred for the microprocessor to be installed on a circuit board (printed circuit board, PCB). In addition to the microprocessor, the PCB also preferably has the heating element and the temperature sensors installed on it. This preferred embodiment allows for an extremely compact and also robust architecture of the device and particularly intelligent temperature regulation using the microprocessor. Thus the microprocessor is not only able to evaluate the measured temperature data and translate it into control of the heating elements, but also it can rapidly and reliably take additional parameters such as error messages and user input into consideration.

In a preferred embodiment of the invention, the device is characterized in that the microprocessor, the heating element and the at least one temperature sensor are installed on a printed circuit board (PCB), wherein at least the heating element and the temperature sensor are coated with a protective lacquer. In the meaning of the invention, a protective lacquer is preferably a lacquer or paint intended to protect components of the PCB from environmental influences. For this purpose the protective lacquer acts as an electrical insulator and is waterproof. The property of electrical insulation can preferably be quantitated based on the surface resistance or surface insulation resistance (SIR). The SIR can preferably be measured, for example, using leakage currents between the components of the conductor plate. A high resistance corresponds to good electrical insulation. Waterproof preferably means that even at high atmospheric humidity or penetration of water, the lacquered electronic components remain intact and no short-circuiting occurs. For example, the water resistance can also be determined by measuring the SIR under conditions of high atmospheric humidity. Numerous protective lacquers preferentially suitable for use are known in the prior art. As examples, protective lacquers based on acrylate, silicone or polyurethane may be mentioned. By applying the protective lacquer in the area of the heating elements and temperature sensors, these are effectively protected from deposits, so that incorrect measurements by the temperature sensors can be avoided. On one hand this increases the accuracy with which the treatment temperature can be adjusted, and on the other hand this avoids overheating of the treatment surface because of inaccurate temperature measurement.

Coating the components mentioned surprisingly makes it possible to achieve reliable additional thermal safeguarding of the device using particularly simple and cost-advantageous technical means. Surprisingly, installation of the components on a PCB has proven especially advantageous for coating the components.

In a preferred embodiment of the invention, the device is characterized in that the device comprises a data memory for storing the system data and/or error messages. Preferred system data include a counter for the treatment cycles, which preferably counts the use of different types of treatment cycles separately. For example, if a shorter or a longer treatment cycle can be selected, this will be counted separately. In addition, the system data preferably comprise a boot counter, i.e., a counter for how many times the device was started up, and information on the error messages with the current error status.

Preferably the following error messages can be stored: "Reset" shows that the voltage controller triggered a reset. "Watchdog" shows that a watchdog reset took place in the firmware, i.e., a system restart based on a software error. Preferably for error reporting it is possible to determine the program mode in which the apparatus was operating when the error occurred. "Temperature too high" can indicate that the temperature measured on the temperature sensor is too high or that the temperature sensor is defective. "Temperature too low" can indicate that the temperature measured on the temperature sensor is too low or that the temperature sensor is defective. "Treatment temperature reached" can indicate whether the desired treatment temperature was reached or an error occurred during the preheating phase.

Advantageously, the stored system data and error messages can be used for diagnosis and treatment of problems for the device. For example, these data can be read out when a customer sends in a defective apparatus. Based on the data it is possible to correlate the error that occurred, e.g., "Temperature too high" with additional system data on the number of treatment cycles or the watchdog resets. Based on these data therefore it is possible to continuously optimize the safety features of the device during the development phase and afterward. The possibility that the device comprises storage of system data and error messages thus permits continuous improvement of the hardware and software components of the based on meaningful data.

In an additional embodiment the device is characterized in that firmware is installed on the control device which at least controls the temperature regulation of the treatment surface, wherein the firmware comprises a watchdog counter (WDC) that monitors whether the firmware is executed. In the meaning of the invention, firmware is preferably defined as software, i.e., the instructions for a computer-implemented process, which is embedded in the control device, preferably in the microprocessor. In other words, the firmware preferably comprises the software that is functionally linked with the hardware of the device, i.e., especially with the heating elements and temperature sensors. Preferably the firmware is run on startup of the device and takes over the monitoring and control function of these hardware components of the device. Thus the control device, preferably based on the firmware, evaluates for example the measurement data of the temperature sensors and user inputs in order to control the current feed for the heating elements during the treatment cycle. In the meaning of the invention, hardware-implemented components are preferably components, the function of which is assured independently of correct execution of the firmware. As described above, the temperature controller is hardware-implemented, so that its function, i.e., limiting the maximum temperature, can take place independently of correct execution of the firmware on the control device. Even in the case of a system failure of the firmware, the hardware-implemented temperature controller therefore can quickly and correctly limit the maximum temperature of the treatment surface.

In the particularly preferred embodiment, the firmware of the control device is monitored with the aid of a hardware-implemented watchdog counter. This is particularly preferably a time-out watchdog. Preferably the time-out watchdog is activated by the firmware before the start of the treatment phase. During the treatment phase, the firmware will send a signal to the time-out watchdog to reset it within a certain predetermined time interval. If the time-out watchdog is not reset, this will preferably lead to restarting of the firmware. The time interval is preferably based on the time projected for carrying out a temperature measurement and regulation of the heating elements by the firmware and can, for example, amount to between 2 ms and 10 ms. Using such a time-out watchdog it can advantageously be confirmed that at least during the treatment phase of the device, the firmware is functioning correctly and the temperature of the treatment surface is being monitored. By using a hardware-implemented watchdog for monitoring the firmware, preferably for example with the aid of a time-out watchdog, it is thus possible to make sure that if the firmware does not function correctly and the predetermined time interval is not maintained, the treatment phase will be interrupted. Thus an additional safety feature of the device in addition to the one mentioned above is present, which especially in interaction with the hardware-implemented temperature ensures that even if the firmware is not functioning correctly, overheating of the treatment surface will be ruled out. Then the safety fuse is present as the final, additional safety step.

This makes sure that the treatment is always carried out with the optimized parameters for hyperthermic treatment, and as an additional safety barrier can protect the treatment surface from overheating.

DESCRIPTION OF THE DRAWING

The drawing: Block diagram of a preferred embodiment of the device

The Drawing shows the block diagram of a preferred embodiment of the device. The treatment surface 1 is heated to the treatment temperature with the aid of at least one heating element The treatment surface 1 is preferably a contact pad made of ceramic or gold. Especially semiconductor elements such as FETs, more preferably MOSFETs, have proven advantageous as heating elements. In addition to their small size, these are characterized by highly dynamic heat generation and release, and a particularly rapid response behavior. The regulation of the temperature of the treatment surface 1 takes place with the aid of a control device 6, which is preferably a microcontroller, and controls the current feed to the heating elements The temperature of treatment surface 1 is monitored with a first temperature sensor 4, which is preferably an NTC thermistor. Based on the temperature measured by the temperature sensor 4, the control device 6 can set the optimal current feed to keep the treatment temperature constant during the desired time period. During the operation of the device, a visual display 7, preferably an LED, and a sound generator 8, preferably a buzzer, shows the user the phase of the treatment cycle. Thus for example at the start of the heating phase, the sound generator 8 can generate a buzzing tone and the optical display 7 can be illuminated. The preferred treatment time is input through the input element 9, which is preferably a pushbutton switch. The various program sequences and the regulation of the temperature of the treatment surface 1 are controlled by the control device. The current or voltage supply of the device is provided by a power supply unit 13, e.g., a battery.

If the control device 6 for controlling the temperature of the treatment surface 1, for example, because of faulty electronics, the hardware-implemented temperature controller will allow the heating elements 2 to be shut off if the maximum temperature is exceeded. For this purpose the device has a second temperature sensor 3, preferably an NTC thermistor, which is connected to comparator 5. If the temperature of the treatment surface 1 rises, the voltage value at the comparator 5, regulated by the second temperature sensor 3, moves toward a voltage reference value that corresponds to a predetermined maximum temperature. As soon as the temperature of the treatment surface 1 exceeds the maximum temperature, the output signal on the comparator 5 changes in a binary manner, interrupting the supply voltage for the heating element 2.

In addition to the hardware-implemented temperature controller, the device also has a safety fuse 11 that functions as an additional safety element. During the treatment phase, in the case of smooth operation, the heating elements 2 draw a defined treatment power from the power supply unit 13. If a defect results in continuous heating of the heating elements 2, the supply current increases greatly. Advantageously, above a maximum current, the safety fuse 11 is triggered. In this way, even in the case of short-circuiting of the device, uncontrolled heating of the treatment surface 1 can be avoided. Advantageously, this safety mechanism will only need to intervene if the temperature regulation both by the control device 6 and by the hardware-implemented temperature controller do not function properly. For further controlling the power supply unit 13, the device also comprises a power supply reverse polarity protector 12 and a voltage controller 10, which is preferably a supply voltage supervisor (SVS).

LIST OF SYMBOLS

1 Treatment surface
2 Heating element(s)
3 Second temperature sensor for the hardware-implemented temperature controller
4 First temperature sensor for regulation by the control device
5 Comparator of the hardware-implemented temperature controller
6. Control device
7 Optical display
8 Sound generator
9 Input element for the treatment time
10 Voltage controller
11 Safety fuse
12 Voltage supply inverse polarity protection
13 Current supply unit

The invention claimed is:

1. A device for hyperthermic treatment of itching comprising:
   at least one treatment surface;
   a control device for regulating a temperature of the at least one treatment surface, wherein the control device is configured to regulate the temperature of the at least one treatment surface by heating at least one heating element in a heating phase to a treatment temperature of between 42° C. and 56° C. and in a treatment phase the control device is configured to maintain the treatment temperature for a period of 2 seconds to 12 seconds;
   a hardware-implemented temperature controller configured to: a) reversibly limit, independently of temperature regulation operation of the control device, a maximum temperature of the at least one treatment surface to a value of between 54° C. and 58° C., b) interrupt a power supply to the at least one heating element during a period in which the temperature of the at least one treatment surface exceeds the maximum temperature, and c) discontinue the interruption as soon as the temperature of the at least one treatment surface falls again below the maximum temperature; and
   a safety fuse configured to shut off the device in case of a short-circuit or uncontrolled continuous heating.

2. The device according to claim 1, further comprising at least one first temperature sensor for measuring a temperature of the at least one treatment surface, wherein the control device is configured to adjust a temperature of the at least one heating element based on measurement data of the at least one first temperature sensor.

3. The device according to claim 1, wherein the hardware-implemented temperature controller comprises at least one temperature sensor for measuring the temperature of the at least one treatment surface and a comparator, wherein the comparator is configured to compare the temperature of the at least one treatment surface with the maximum temperature, and if the maximum temperature is exceeded, to stop a current feed to the at least one heating element.

4. The device according claim 1, wherein the safety fuse has a threshold value for a maximum current which corresponds to the heating of the at least one treatment surface to 65° C. for 1 second.

5. The device according to claim 1, wherein a threshold value of the safety fuse is between 1 A and 2.5 A.

6. The device according to claim 1, wherein the at least one treatment surface comprises ceramic and/or gold.

7. The device according to claim 1, wherein the at least one treatment surface is surrounded by a marker that lights up during a treatment cycle.

8. The device according to claim 1, further comprising an optical display and/or a sound generator that indicates a start of the heating phase, the reaching of the treatment temperature, a duration of the treatment phase and/or an end of the treatment phase with an acoustic and/or optical signal.

9. The device according to claim 1, further comprising a watertight housing.

10. The device according to claim 1, further comprising a power supply unit and a voltage controller that monitors voltage of the power supply unit.

11. The device according to claim 1, wherein the control device comprises at least one microprocessor.

12. The device according to claim 1, further comprising at least one temperature sensor for measuring a temperature of the at least one treatment surface and a printed circuit board; wherein the control device comprises a microprocessor and the at least one heating element and at least one temperature sensor are installed on the printed circuit board, and wherein at least the at least one heating element and the at least one temperature sensor are coated with a protective lacquer.

13. The device according to claim 1, further comprising a data memory for storing system data and/or error messages.

14. The device according to claim 1, wherein firmware is installed on the control device which is configured to be launched when the device is started up and is configured to at least guide a temperature regulation of the at least one treatment surface; and wherein the control device comprises a hardware-implemented watchdog counter configured to monitor whether the firmware is executed.

\* \* \* \* \*